United States Patent [19]
Wang et al.

[11] Patent Number: 6,011,082
[45] Date of Patent: Jan. 4, 2000

[54] PROCESS FOR THE MODIFICATION OF ELASTOMERS WITH SURFACE INTERPRETING POLYMER NETWORKS AND ELASTOMERS FORMED THEREFROM

[75] Inventors: Yading Wang, Mission Viejo, Calif.; Robert van Boxtel, Wierden, Netherlands; Stephen Q. Zhou, Irvine, Calif.

[73] Assignee: Pharmacia & Upjohn AB, Stockholm, Sweden

[21] Appl. No.: 08/867,269

[22] Filed: Jun. 2, 1997

[51] Int. Cl.[7] .............................. C08G 77/04; G02C 7/04
[52] U.S. Cl. .................... 523/107; 523/106; 523/105; 525/54.2; 525/903; 427/2.24; 427/164; 514/56; 514/802; 623/6; 424/429
[58] Field of Search ..................... 523/106, 107, 523/105; 525/903, 54.2; 623/6; 424/429; 427/2.24, 164; 514/56, 802

[56] References Cited

U.S. PATENT DOCUMENTS

| | | | |
|---|---|---|---|
| 4,423,099 | 12/1983 | Mueller et al. | 525/903 |
| 4,563,490 | 1/1986 | Stol | 523/106 |
| 5,135,297 | 8/1992 | Valint, Jr. | 351/166 |
| 5,426,158 | 6/1995 | Mueller et al. | 525/455 |
| 5,529,986 | 6/1996 | Larsson et al. | 424/422 |
| 5,607,475 | 3/1997 | Cahalan et al. | 427/2.24 |
| 5,645,882 | 7/1997 | Llanos | 427/2.24 |
| 5,679,659 | 10/1997 | Verhoeven et al. | 514/56 |

FOREIGN PATENT DOCUMENTS

| | | |
|---|---|---|
| 0430082 | 11/1990 | European Pat. Off. . |
| 0643083 | 9/1994 | European Pat. Off. . |

*Primary Examiner*—Andrew E. C. Merriam
*Attorney, Agent, or Firm*—Oppenheimer, Wolff & Donnelly, LLP

[57] ABSTRACT

A process for forming a surface modification on a polymer substrate and polymer substrates having such surface modifications. The process comprises the steps of absorbing a swelling monomer into the polymer substrate for a period of time in order to swell the polymer substrate; removing the swollen polymer from the swelling monomer; transferring the swollen polymer to a reaction mixture containing at least one functional monomer; polymerizing the functional monomer in the reaction mixture containing the swollen polymer substrate for a period of time; and removing the polymer from the reaction mixture. Because the surface modification produced by the process is a surface interpenetrating polymer network, the process is not sensitive to the reactive groups located on the surface of the polymer substrate. Further, the surface interpenetrating network bonds to the polymer substrate through caternary connections or other forms of chain entanglement and thus is quite stable. Polymer substrates having the surface modification of the present invention are capable of having a surface modification agent, such as heparin, adhere to the surface of the polymer substrate.

8 Claims, 4 Drawing Sheets

ATRIR FOR SILICONE SUBSTRATE MODIFIED
BY THE PROCESS OF THE PRESENT INVENTION
THEN EXTRACTED IN ETHANOL

PROCESS FOR THE MODIFICATION OF ELASTOMERS WITH SURFACE INTERPRETING POLYMER NETWORKS AND ELASTOMERS FORMED THEREFROM

FIELD OF THE INVENTION

This invention relates in general to a process for forming a surface modification on a polymer and relates in particular to a process for forming a surface interpenetrating polymer network on polymers and to the polymers having such surface interpenetrating polymer networks.

BACKGROUND OF THE INVENTION

Polymers are often used in medical device applications due to the fact that they are easy to process, they have good mechanical properties, and they have an acceptable level of biocompatability. In certain medical device applications, the surface of the polymer will be in contact with the cells and fluids of the body. In these applications, it is necessary that the surface of the polymer have certain beneficial properties in order to be in contact with the cells and fluids of the body. In certain applications and with certain polymers, the surface of the polymer will not embody these certain beneficial characteristics. In such cases, it may be necessary to modify a thin surface layer of the polymer so that it may embody these beneficial characteristics, while at the same time maintaining the beneficial characteristics of the bulk properties of the polymer.

Numerous types of polymer surface modifications and methods for preparing such modifications are known. Such existing surface modification methods on polymers include gas plasma, radiation grafting, photoinduced grafting, sol-gel process, surface etching, and polyamine adsorption. Although these existing surface modification techniques are adequate for their purposes, they each have their drawbacks. For instance, the gas plasma technique tends to yield non-uniform surfaces on polymers such as silicone, which would increase, rather than reduce, cell adhesion. Ionizing radiation may weaken and discolor the polymer material, which is a significant drawback with silicone intraocular lenses. In photoinduced grafting, a coupling agent reacts directly with the polymer substrate surface, and thus the process is sensitive to the particular reactive groups located on the surface of the polymer substrate. The sol-gel process creates a modified surface that lacks long-term stability. Surface etching cleaves the polymer backbone, which may weaken the surface structure of the polymer.

Another method of making a surface modification to a polymer is to chemically bond a coupling agent directly to the surface of the polymer. This method requires that the coupling agent bond directly to a reactive group on the surface of the polymer substrate. Thus, because the coupling reaction is dependent on the reactive groups located on the surface of the polymer substrate, the particular reaction conditions and coupling agents will be dependent on the particular reactive group.

Another known surface modification technique is the use of bulk interpenetrating polymer networks. An interpenetrating polymer network is a combination of two polymers in the network form, at least one of which is polymerized in the presence of the other. Bulk interpenetrating polymer networks are synthesized by polymerization throughout the bulk of the polymer. For instance, European Patent No. 643,083 discloses a bulk interpenetrating polymer network from polydimethylsiloxane and polyacrylic acid for fabricating soft contact lenses. Further, U.S. Pat. No. 5,426,158 discloses contact lenses made from a bulk interpenetrating polymer network.

The bulk interpenetrating polymer networks, although adequate for their intended use, have drawbacks of their own. For instance, in bulk interpenetrating polymer networks, the polymerization initiator is uniformly distributed throughout the bulk of the polymer to be modified. Polymers that have bulk interpenetrating polymer networks formed therein have different physical properties than the same polymer without the bulk interpenetrating polymer networks, because networks are created throughout the entirety of the polymer. Thus, for example, an untreated clear polymer that has a bulk interpenetrating polymer network may be cloudy throughout, and thus not suitable for an optical application. Further, in polymers having bulk interpenetrating polymer networks, the functional monomers used in the polymerization process are mixed into the entire bulk of the polymer, and therefore only part of these molecules are available for functioning on the surface of the polymer.

Accordingly, it will be appreciated from the foregoing that there is a definite need for a process whereby the surface of a polymer can be modified to have certain desired properties, while at the same time maintaining the desirable physical properties of the polymer. One of the desired properties resulting from the surface modification should be the ability of the surface of the polymer to couple with a surface modification agent, such as heparin. The process should provide for an interpenetrating polymer network which occurs only on the surface of the polymer, rather than in the bulk of the polymer. The coupling agent of the interpenetrating polymer network should not be chemically bound to any reactive groups on the polymer substrate so that the process of forming the surface modification is not sensitive to the particular reactive groups located on the polymer substrate. Further, the process should yield uniform surfaces on the polymer, should not weaken or discolor the polymer material, should be relatively simple and inexpensive, and should provide a surface modification that has long-term stability. The present invention meets these needs.

SUMMARY OF THE INVENTION

In accordance with the present invention, a process for forming a surface modification on a polymer is provided. The process modifies the properties of the polymer at its surface. The process can be used to increase the ability of a surface modification agent, such as heparin, to adhere to the surface of the polymer. The surface of the polymer is modified by a surface interpenetrating polymer network, which provides for the indirect bonding of the polymer network with the surface of the polymer substrate in a caternary connection or other form of chain entanglement. There are no direct bonds to any reactive groups located on the surface of the polymer substrate, so the process is not sensitive to the particular reactive groups located on the surface of the polymer substrate. Further, the surface modification of the present invention affects only the surface of the polymer, rather than the bulk of the polymer. Thus, the desirable physical properties of the bulk polymer are maintained. The process also yields uniform surfaces on the polymer, does not weaken or discolor the polymer material, is relatively simple and inexpensive, and provides a surface modification that has long-term stability.

The present invention provides a process for the surface modification of a polymer involving the use of surface interpenetrating polymer networks. An interpenetrating polymer network is a combination of two polymers in the network form, at least one of which is polymerized in the immediate presence of the other. An interpenetrating polymer network is distinguished from simple polymer blends, blocks, or grafts in two ways: (1) an interpenetrating polymer network swells, but does not dissolve in solvents, and (2) creep and flow are suppressed.

In general, the interpenetrating polymer networks of the present invention are prepared by the introduction of a swelling monomer into the surface of a polymer substrate in order to swell the polymer substrate at its surface. The swelling occurs in a solvent, although the solvent may not always be necessary, because the monomer should be able to diffuse into the substrate surface with or without the aid of a solvent. The swelling process occurs at a particular temperature and for a particular time period. The swelling monomer is then catalyzed in the presence of an initiator that has been introduced into the reaction mixture. The swelling monomer may be a crosslinking monomer, a functional monomer, or a combination of both.

In another embodiment of the present invention, the polymer substrate may be removed from the surface modification process of the present invention following swelling and placed in a reaction medium containing a functional monomer, and, in some cases, a solvent. The functional monomer is then polymerized in a polymerization reaction which may be initiated by a catalyst, or by UV radiation, heat, or ionization radiation. The polymerization of the swelling monomer and the functional monomer occurs at a particular temperature for a particular period of time. Upon initiation, polymerization proceeds in the solution resulting in a soluble polymer. On the surface of the polymer, however, the polymerization results in an interpenetrating polymer network due to the presence of the swelling monomer, which polymerizes together with the functional monomer at the surface interface of the polymer substrate.

The surface interpenetrating network formed on the polymer substrate is quite stable. The bonding between the functional monomer and the polymer is indirect, in that catenary connection and other forms of chain entanglement are responsible for the bonding of the coupling agent and the polymer. Because the functional monomer does not chemically react with the substrate, this interpenetrating polymer network process is rather insensitive to the substrate surface, as long as the surface swells to a certain extent. Thus, in order to break the surface interpenetrating polymer network, a covalent bond on the interpenetrating polymer must be broken. Even if such a covalent bond is broken, the interpenetrating polymer will still be entrapped within the surface of the polymer substrate and thus the surface modification to the polymer substrate will remain virtually intact.

The surface modification process of the present invention is useful for modifying the surface of a silicone polymer. Thus, silicone intraocular lenses, silicone contact lenses, silicone particles for a chromatography column, and other medical devices may be formed. Further, the surface modification process is useful for permitting a surface modification agent, such as heparin, to adhere to the surface of a silicone lens having the surface interpenetrating polymer network of the present invention, for instance.

Other objects, features, and advantages of the present invention will become apparent from a consideration of the following detailed description.

DETAILED DESCRIPTION OF THE PREFERRED EMBODIMENTS

Figure 1:
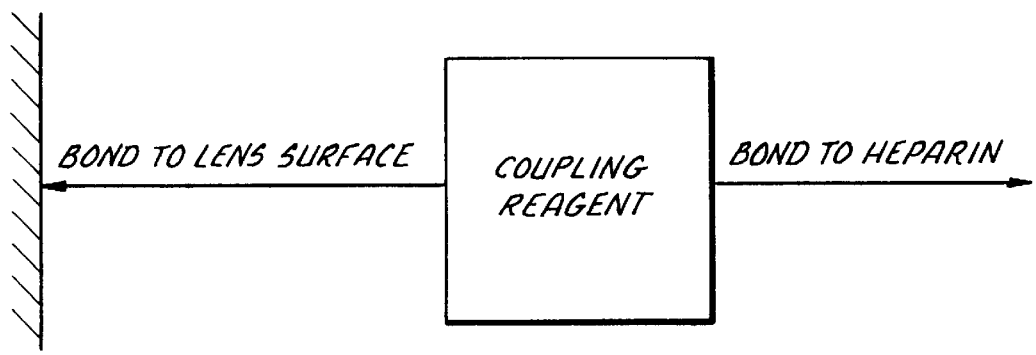
FIG. 1 is a diagram showing the traditional surface modification method of bonding one end of a coupling agent to a reactive group on a silicone lens surface.

The present invention is embodied in a process for providing a surface modification to a polymer in the form of an interpenetrating polymer network on a polymer substrate. The process is useful in that it can be used to increase the ability of a surface modification agent, such as heparin, to adhere to the surface of the polymer. The surface interpenetrating polymer network provides for the indirect bonding of the polymer network with the surface of the polymer substrate in a caternary connection or other form of chain entanglement. Because there is no direct reaction with the reactive groups of the polymer substrate, the process of the present process is not sensitive to the particular reactive groups located on the surface of the polymer substrate. Further, the surface modification of the present invention affects only the surface of the polymer, rather than the bulk of the polymer. Thus, the desirable physical properties of the bulk polymer are maintained. The process also yields uniform surfaces on the polymer, does not weaken or discolor the polymer material, is relatively simple and inexpensive, and provides a surface modification that has long-term stability.

In accordance with the present invention, a polymer substrate is provided on which the surface interpenetrating polymer network will be formed. The polymer is preferably any polymer that may be swelled by the absorption of a monomer, with or without the aid of a solvent. The polymers used in the present invention are preferably selected from the group consisting of acrylics, acrylonitrile-butadienestyrene copolymer, chlorinated polyvinylchloride, EPDM rubber, natural rubber, neoprene, nitrile rubber, polyethylene, polypropylene, polystyrene, polyurethanes, polyvinylchloride, silicones, thermoplastic elastomers; and vinylidene fluoridehexafluoropropylene copolymer.

Generally, the surfaces of these polymers, in their untreated state, are hydrophobic. As used herein, hydrophobic means that the contact angle of a drop of water on the surface of the polymer is greater than 90°. A contact angle of less than 90° means that the surface of the polymer is hydrophilic. For instance, silicone has a typical contact angle of about 100° to 110°. After undergoing the surface modification process of the present invention, the surface of the treated silicone has a contact angle of less than 90°, and may be as low as 40°. As used herein, contact angles and their measurement are described in Adamson, *Physical Chemistry of Surfaces*, John Wiley & Sons, at pages 341–343 (1982).

The surface modification process of the present invention starts with a controlled absorption of a swelling monomer into the surface of the polymer substrate. The swelling monomer preferably comprises either at least one crosslinking monomer, at least one functional monomer, or the combination of at least one of each. The swelling monomer preferably contains at least a di- or multi-functional agent. The swelling monomer used in accordance with the present invention is preferably chosen from the group consisting of acrylamides, acrylates, styrenic, methacrylamides, allyl crosslinkers, methacrylates, and vinyl crosslinkers.

The absorption of the swelling monomer into the polymer substrate may be carried out in the presence of a solvent. Even if no solvent is used, the swelling monomer may consist of one or more monomers, the monomers being either crosslinking monomers, functional monomers, or a combination of both. For each particular polymer substrate utilized in accordance with the present invention, there is a corresponding preferred type of solvent, as shown below in Table 1:

TABLE 1

Types of Preferred Solvents for Each Preferred Polymer Substrate

| SUBSTRATE | TYPE OF SOLVENT |
| --- | --- |
| acrylics | benzene and derivatives, chlorinated hydrocarbons, alcohols, dioxane, ketones, acetic acid, acetates, isobutyric acid |
| acrylonitrile-butadiene-styrene copolymer | amines, anhydrides, ketones, DMF, DMSO, DMA, ethylene oxalate, ethylene carbonate, 2-oxazolidone, cyanoacetic acid, sulfones |
| chlorinated polyvinylchloride | aromatic hydrocarbons, chlorinated hydrocarbons, THF, dioxane, ketones, acetates, nitrobenzene, DMF, DMSO |
| EPDM rubber | hydrocarbons, halogenated hydrocarbons, aliphatic esters and ketones, ethers, acetates |
| natural rubber | benzene, halogenated hydrocarbons, hydrocarbons, THF, ketones, esters, ethers |
| neoprene | benzene, halogenated hydrocarbons, hydrocarbons, THF, ketones, esters, ethers |
| nitrile rubber | benzene, halogenated hydrocarbons, hydrocarbons, THF, ketones, esters, ethers |
| polyethylene | hydrocarbons, halogenated hydrocarbons, aliphatic esters and ketones, ethers, acetates |
| polypropylene | hydrocarbons, halogenated hydrocarbons, aliphatic esters and ketones, ethers, acetates |
| polystyrene | hydrocarbons, chlorinated hydrocarbons, aromatic hydrocarbons, ethers, ketones, acetates |
| polyurethanes | phenol, m-cresol, formic acid |
| polyvinylchloride | aromatic hydrocarbons, chlorinated hydrocarbons, THF, dioxane, ketones, acetates, nitrobenzene, DMF, DMSO |
| silicones | hydrocarbons, aromatic and halogenated hydrocarbons, hydrogenated xylene, 1,2-dimethoxyethane, phenetole, octylamine, ketones, acetates |
| thermoplastic elastomers | hydrocarbons, halogenated hydrocarbons, esters and ketones, ethers, acetates |
| vinylidene fluoride-hexafluoropropylene copolymer | cyclohexanone, butyrolactone, ethylene carbonate, DMA, N-methylpyrrolidone, DMSO, hexafluorobenzene, perfluorodibutyl ether, perfluorodibutylamine |

The absorption of the swelling monomer into the polymer substrate in the presence of a solvent should be sufficient to diffuse into and swell the polymer substrate such that the swelling monomer will diffuse into the polymer in a gradient. The swelling of the polymer by the swelling monomer opens and exposes interstices in the polymer.

The polymer substrate is preferably swelled at a temperature of between approximately −20° C. to 150° C. for a time period of between approximately 0 to 96 hours.

In one embodiment of the present invention, the swelling monomer is polymerized after the swelling step of the process has been completed. The swelling monomer is preferably polymerized in the presence of an initiator. The types of initiators used, and the polymerization reaction conditions are discussed in more detail below.

In another embodiment of the present invention, the swollen polymer is transferred into an solution containing a functional monomer and an initiator, after the polymer substrate has undergone the swelling step. This solution is also known as the interfacial reaction medium or the reaction mixture. The interfacial reaction medium may contain a solvent, but a solvent need not always be present.

It is within the interfacial reaction medium that the polymerization reaction of the swelling monomer and functional monomer occurs. The polymerization reaction is preferably carried out at temperatures of between approximately −78° C. to 150° C. for a period of time of between approximately 10 seconds to 72 hours.

A number of different functional monomers may be used in accordance with the present invention to polymerize with the swelling monomer. Functional monomers having at least one amine, hydroxyl, or carboxyl groups are preferred. For example, the preferred functional monomers are chosen from the group consisting of acrylamides, methacrylamides, acrylates, methacrylates, allyl monomers, vinyl monomers, and styrenic monomers.

In addition to the monomers listed above, oligomers or polymers having similar polymerizable functions to the monomers listed above may also be used in accordance with the present invention.

If necessary, the polymerization reaction with the functional monomer (or, as discussed above, the polymerization of the swelling monomer) is initiated by a form of an initiator. Some of monomers and crosslinkers utilized in the process are thermo- or photo-sensitive. In processes using these thermo- or photo-sensitive monomers and/or crosslinkers, the polymerization can be initiated with ultraviolet light or heat. Further, the polymerization reaction may be initiated by ionizing radiation. In other processes, the polymerization is initiated by a catalyst initiator. For monomers where a catalyst initiator is used, the catalyst initiator is preferably present in the interfacial reaction medium in a concentration from between approximately 0.01% to 10%.

A solvent may also be present in the interfacial reaction medium. The solvent used in the interfacial reaction medium is preferably the solvent indicated above in Table 1 for the specific polymer substrate being used. The solvent provides the benefit of being able to increase the depth of the interpenetrating polymer network in the polymer substrate.

Upon initiation, polymerization proceeds in the solution, creating a soluble polymer. On the polymer surface, however, the polymerization results in an interpenetrating polymer network due to the presence of the crosslinker. The mutual solubility of the two solvents must be low, so that the polymerization takes place only at the surface/interface of the solvent systems.

In cases where a catalyst initiator is utilized (i.e. where the functional monomer and/or swelling monomer are not thermo- or photo-sensitive and where ionizing radiation is not utilized), the initiator is preferably chosen from the group consisting of azo-initiators, peroxide initiators, and UV/visible initiators.

The following are exemplary of the process of the present invention for forming the surface interpenetrating polymer network on a polymer substrate:

EXAMPLE 1

A silicone sheet is swollen in ethylene glycol dimethacrylate for 15 hours at room temperature. The sheet is then transferred into an aqueous solution containing 2-aminoethyl methacrylate hydrochloride (20%) and 2,2'-azobis(2-methylpropionamidine) dihydrochloride (0.5%). The reaction is carried out at 60° C. for 1.5 hours. A contact angle of 72° is obtained on the modified silicone sheet.

EXAMPLE 2

A silicone sheet is swollen in bis(2-methacryloxyethyl) phosphate for 15 hours at room temperature. The sheet is then transferred into an aqueous solution containing 2-aminoethyl methacrylate hydrochloride (20%) and 2-hydroxy-2-methyl-1-phenylproponone (1%). The reaction is carried out at room temperature for 10 minutes with UV radiation (366 nm, medium intensity). A contact angle of 58° is obtained on the modified silicone sheet.

EXAMPLE 3

An AcrySof intraocular lens (a brand of soft acrylic lens made by Alcon Laboratories), having a contact angle of 47°, was immersed in bis(2-methacryloxyethyl) phosphate for 1 hour, then in water for 20 minutes. The lens was then placed in an aqueous solution containing 20% 2-aminoethyl methacrylate hydrochloride and 1% 2-hydroxy-2-methyl-1-phenyl-1-propanone. The lens containing solution was irradiated with 366 nm UV for 10 minutes. The contact angle was measured at 56° before extraction and 72° after extraction.

In each of the three above-mentioned examples, the silicone substrate material that has undergone the processes is ready for heparinization.

The surface interpenetrating polymer networks created by the process of the present invention provide numerous benefits. For instance, the process provides the benefit of versatility in that monomers with different functionalities may be used to form the polymer network, such as those with at least one amine, hydroxyl, and/or carboxyl group. Thus, these groups can become a part of the surface of the polymer, thereby permitting adhesion to these added groups by a surface modification agent, such as the adhesion of heparin to an amine group at the surface of the polymer.

Further, the surface modification of the present invention provides benefits over the traditional surface modifications. Traditionally, a coupling reagent is bonded directly to the surface of the polymer substrate, as shown in FIG. 1. Thus, there is a covalent bond between the coupling agent and one of the reactive groups on the surface of the polymer substrate. The reaction of the coupling agent with the reactive group of the polymer substrate will require certain reaction conditions depending on the coupling agent and on the polymer substrate. In other words, the surface modification is substrate sensitive, because the reaction conditions and the coupling agent will vary depending on the polymer substrate used. The traditional method is relatively stable, in that the method provides a covalent bond between the coupling agent and the polymer substrate surface which may be difficult to break. If, however, this one covalent bond between the coupling agent and the surface of the polymer substrate is broken, then that coupling agent molecule is lost as a surface modification.

Figure 2:
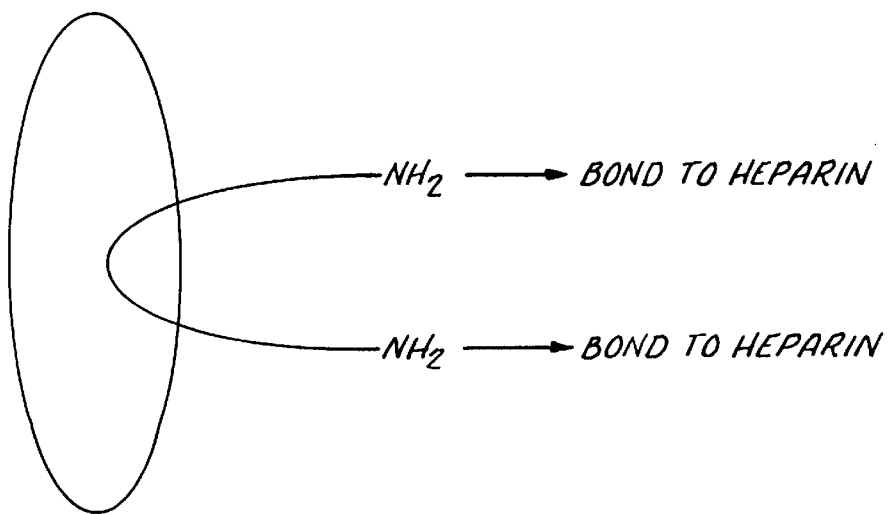
FIG. 2 is a diagram showing one of the surface interpenetrating polymer network molecules of the present invention.

In the present invention, the polymers of the surface interpenetrating network do not bond to the polymer substrate. Instead, the polymer indirectly bonds with the substrate, through catenary connection and other forms of chain entanglement. Since the coupling agent does not bond directly to the substrate, the interpenetrating polymer network is rather insensitive to the substrate surface, as shown in FIG. 2. Further, the surface interpenetrating polymer network of the present invention is also quite stable. In order to break the interpenetrating polymer from the surface of the polymer substrate, a covalent bond in the interpenetrating polymer itself must be broken. If such a bond is broken, however, the remainder of the interpenetrating polymer will remain entangled with the polymer substrate. Thus, the surface interpenetrating polymer network of the present invention is even more stable than the traditional method for surface modification, because, even if a covalent bond in the interpenetrating polymer is broken, the remainder of the interpenetrating polymer will remain entangled within the polymer substrate and be available as a surface modification.

Figure 3:
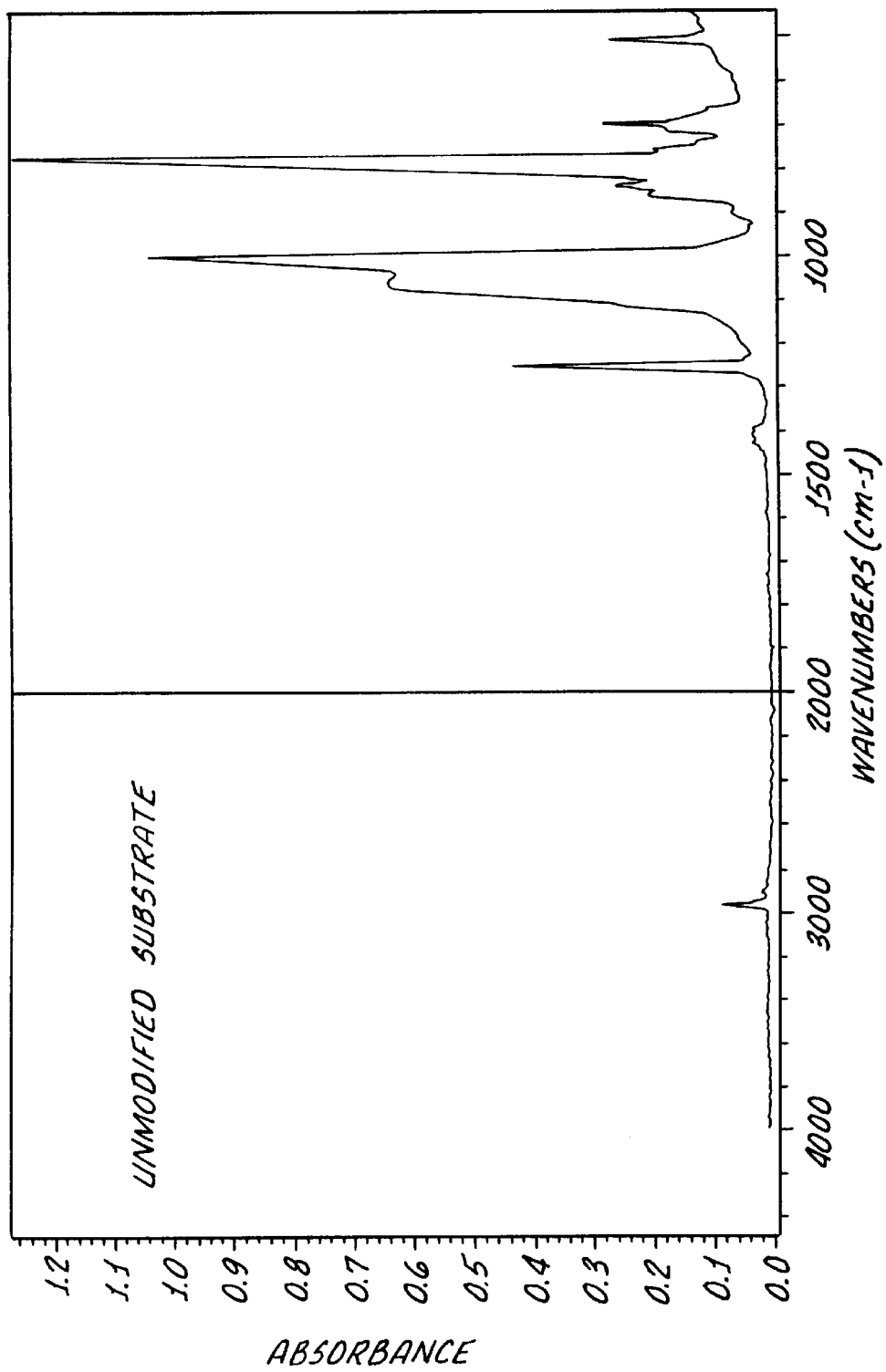
FIG. 3 is a graph showing the attenuated total reflectance infrared spectrum (ATRIR) for an unmodified silicone substrate.

The stability of the interpenetrating polymer network has been proven in a substrate through the use of attenuated total reflectance infrared or ATRIR. ATRIR reveals the surface structure of a material. For instance, FIG. 3 shows the ATRIR spectra for an unmodified silicone substrate for use in the present invention. These are the IR absorption peaks for the silicone substrate.

Figure 4:
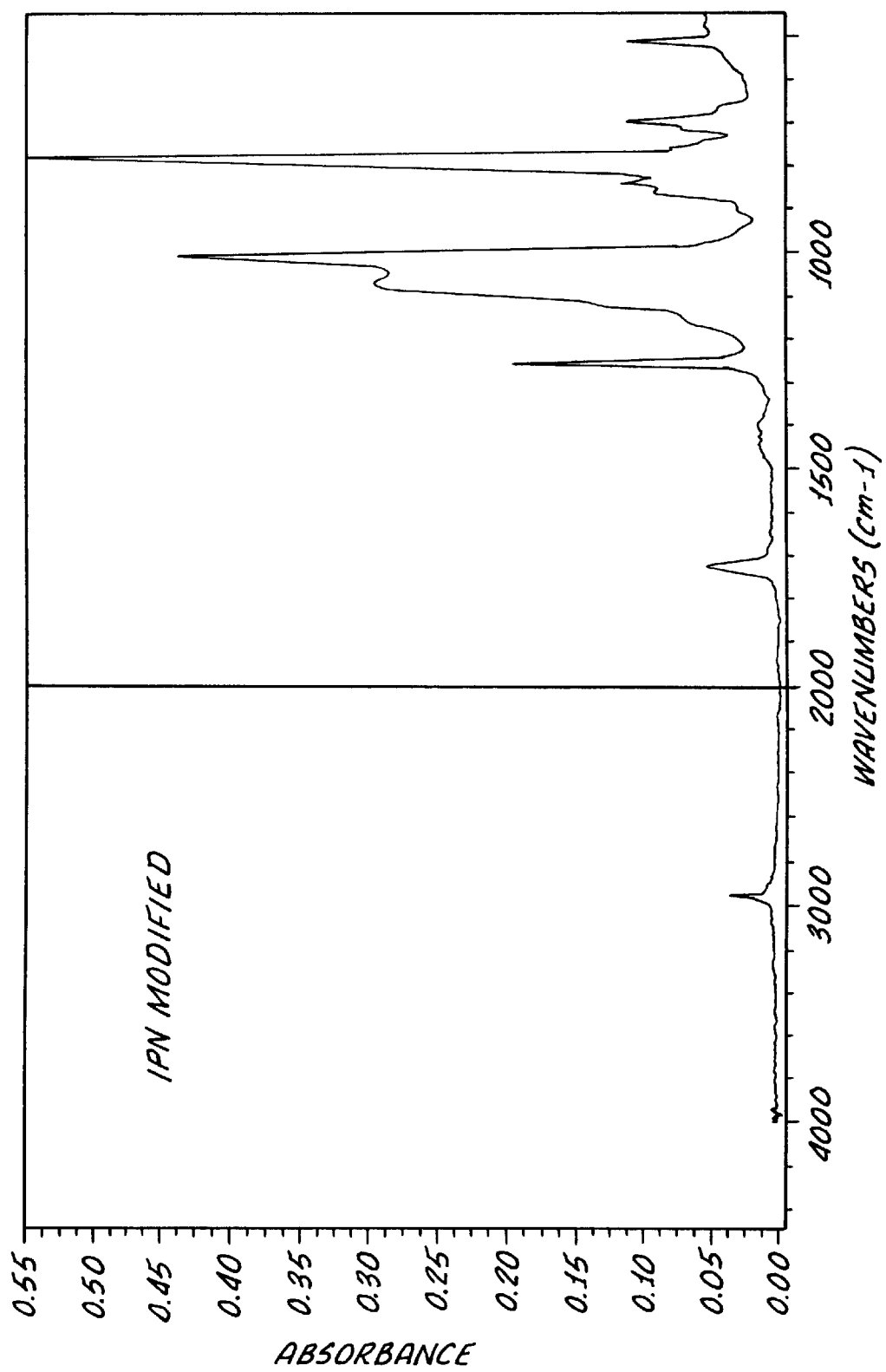
FIG. 4 is a graph showing the attenuated total reflectance infrared spectrum (ATRIR) for a silicone substrate modified by the process of the present invention.

FIG. 4 is a graph which shows the ATRIR for the silicone substrate after it has undergone the interpenetrating polymer network process of the present invention. The IR absorption peaks for the silicone following the process of the present invention shows not only the substrate peaks, but also a new peak at about 1725 $cm^{-1}$, which is the carbonyl stretching peak of the interpenetrating polymer network.

Figure 5:
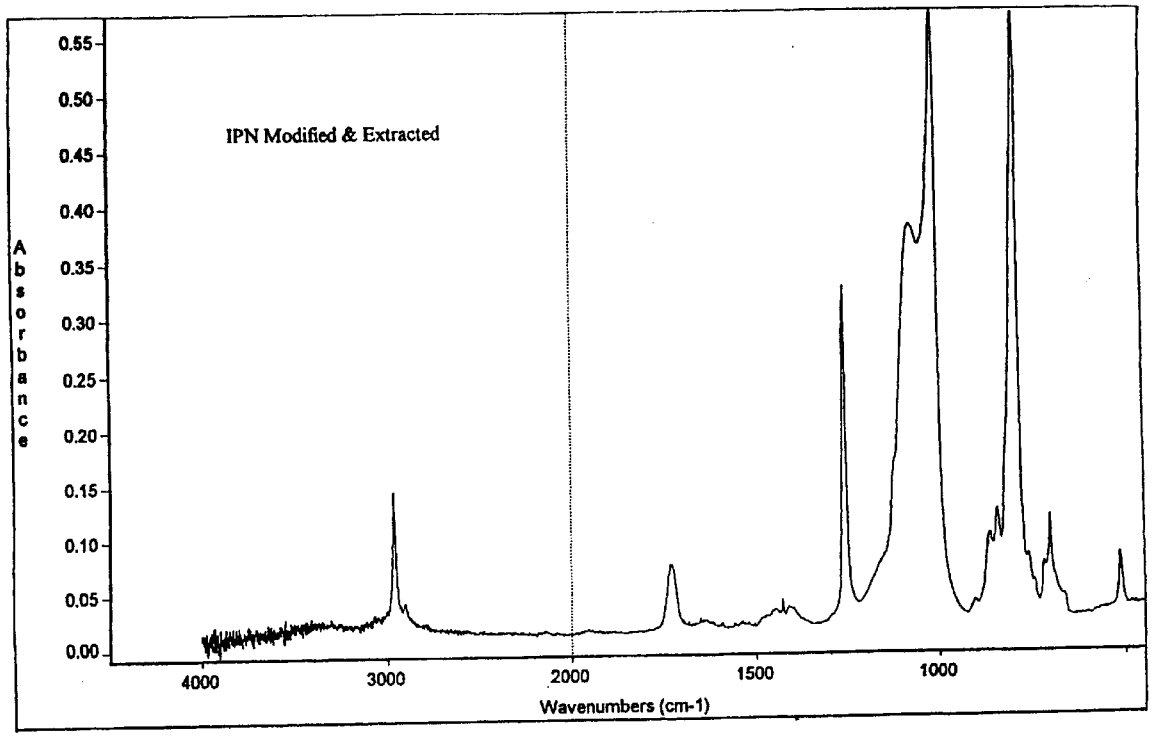
FIG. 5 is a graph showing the attenuated total reflectance infrared spectrum (ATRIR) for a silicone substrate modified by the process of the present invention that has been extracted with ethanol for three days.

In order to prove the stability of the interpenetrating polymer network on the silicone substrate, the treated silicone substrate shown in FIG. 4 was extracted with ethanol for three days at room temperature. The ATRIR for the extracted silicone substrate with the interpenetrating polymer network is shown in FIG. 5. The carbonyl stretching peak of the unextracted silicone shown in Graph 2 is still present in FIG. 5 for the extracted silicone substrate. The continued presence of this peak in the ATRIR indicates the permanent nature of the interpenetrating polymer network in the silicone substrate.

Another benefit of the surface modification of the present invention is that the surface modification may be coupled with a surface modification agent, such as heparin. Heparinization of the polymer substrate having the surface interpenetrating polymer network of the present invention may be carried out as shown in the following example.

EXAMPLE 4—Heparinization of a Substrate

Having an Interpenetrating Polymer Network

In this example, the heparin solution is prepared as follows. To 100 ml of deionized water, 0.25 g of heparin sodium (Sigma Catalog Number H7405) and 1.0 g of citric acid are added. The pH is adjusted to between approximately 2 and 5, but 3.8 is preferred, with 5M NaOH. Added to the heparin solution is 0.016 g of NaCNBH3. The polymer substrate material that has previously been treated with the interpenetrating network process of the present invention is then added to this solution. The reaction is carried out at 50° C. for 2 hours. The polymer material is then rinsed with deionized water and 0.025M sodium borate solution. The polymer substrate has now been heparinized.

The polymer substrate may then be heparinized a second time. The polymer material that was treated with the first heparinization is placed in a 0.025M sodium borate solution with 0.6% polyethylenimine for 1 hour at room temperature. The material is removed and rinsed with deionized water. The material is then transferred back to the heparin solution and the reaction is carried out at 50° C. for 3 hours. The samples are then rinsed with 0.025M sodium borate solution and deionized water. After the second heparinization, the material has a typical contact angle of 20°.

The surface interpenetrating polymer network of the present invention differs from and provides benefits over a bulk interpenetrating polymer network. For instance, in a bulk interpenetrating polymer network, the initiator for the bulk polymerization is distributed in the bulk of the polymer. In the surface interpenetrating polymer network of the present invention, however, the initiator is another phase, i.e., an aqueous phase, and thus the initiator is limited to the surface of the polymer. A polymer treated with a bulk interpenetrating polymer network has different properties than an untreated polymer, because the polymer has a second polymer network in its bulk. These different properties, which may occur in the bulk process, have their drawbacks in that these different bulk properties may cause a polymer such as silicone to become cloudy or hard, which reduce its ability to be used for optical purposes. A polymer treated with the surface interpenetrating polymer networks of the present invention, however, maintains its bulk properties, because the only modification occurs at the surface. Thus, a silicone polymer having a surface interpenetrating polymer network may be sufficiently transparent for optical applications due to the thinness of the surface interpenetrating polymer network. Moreover, in the bulk interpenetrating polymer network, the functional monomer is mixed in the bulk and thus only part of the functional monomers are available for functioning on the surface the bulk interpenetrating polymer network. On the other hand, in the surface interpenetrating polymer network of the present invention, the functional monomers are available for functioning on the surface of the polymers. This is due to the fact that the functional monomer is in the aqueous phase during reaction and thus attach only to the polymer surface during polymerization and remain on the outer layer of the polymer following reaction.

Numerous useful articles may be formed using the process of the present invention. For instance, one useful application of the process is the surface modification of a silicone intraocular lens, which permits the heparinization of the lens surface. Further, a silicone contact lens or a silicone particle for use in a chromatography column may be made using the surface interpenetrating polymer process of the present invention.

While a particular form of the invention has been described, it will be apparent that various modifications can be made without departing from the scope of the invention. Accordingly, it is not intended that the invention be limited by the specific embodiment disclosed in the drawings and described in detail hereinabove.

We claim:

1. A process for producing an ocular lens by modifying the surface of a polymer substrate to provide a semi-interpenetrating polymer network therein suitable for coupling with a surface modification agent, said process comprising the steps of:

absorbing a swelling monomer into the surface of a silicon polymer substrate to swell said silicon polymer substrate surface;

polymerizing said absorbed swelling monomer within said polymer substrate surface to produce an semi-interpenetrating network of polymerized swelling monomer having free ends including reactive functional groups extending from said surface wherein said swelling monomer is selected from the group consisting of: reactive functional acrylamindes, substituted reactive functional acrylamides, reactive functional acrylates, substituted reactive functional acrylates, reactive functional allyl crosslinkers, and reactive functional vinyl crosslinkers;

bonding a surface modification agent to said extending functional groups.

2. The process of claim 1 wherein said functional groups are selected from the group consisting of: amines, amides, carbonyl groups and carboxyl groups.

3. The process of claim 1 wherein said polymerization of said swelling monomer is initiated by either heat, ultraviolet radiation, ionizing radiation, or a chemical catalyst.

4. The process of claim 3 wherein said chemical catalyst is selected from the group consisting of azo-initiators, peroxide initiators, and UV/visible initiators.

5. The process of claim 3 wherein said initiator is present at a concentration of 10% or less.

6. The process of claim 1 wherein said polymerization step is carried out for a period of time ranging from approximately 10 seconds to 72 hours and at a temperature of between approximately −78° C. to 150° C.

7. The process of claim 1 wherein said surface modification agent is heparin.

8. A heparinized silicone lens formed by the process of claim 7.

* * * * *